United States Patent [19]
Henningsen

[11] Patent Number: 6,005,011
[45] Date of Patent: Dec. 21, 1999

[54] PROCESS FOR CONVERTING GAS TO LIQUIDS

[75] Inventor: Gunnar Henningsen, Richmond, Tex.

[73] Assignee: The M. W. Kellogg Company, Houston, Tex.

[21] Appl. No.: 09/073,685

[22] Filed: May 6, 1998

[51] Int. Cl.⁶ .............................. C07C 27/00; C07C 1/02
[52] U.S. Cl. .................... 518/706; 518/700; 518/701; 518/702; 518/703; 518/728; 252/373
[58] Field of Search ..................................... 518/701, 703, 518/702, 706, 728, 700; 252/373

[56] References Cited

FOREIGN PATENT DOCUMENTS

WO93/06041  4/1993  WIPO .
WO 97/12118  4/1997  WIPO .

OTHER PUBLICATIONS

Hedden, K et al, Erdoel, Erdgas, Kohle (1994), 110 (7/8), 318–321, Jul. 1994.

*Primary Examiner*—Paul J. Killos
*Assistant Examiner*—J. Parsa
*Attorney, Agent, or Firm*—Kellogg Brown & Root, Inc.

[57] ABSTRACT

A plant and process for converting associated gas from crude oil to methanol at or near the wellhead. The process uses partial oxidation of the associated gas, direct quench, liquid phase methanol conversion wherein substoichiometric $H_2:CO$ is converted to methanol, and a loop purge to a gas turbo generator to provide all of the plant power requirements. This results in avoiding a complex vapor phase, multiple reactor methanol loop and steam-catalytic reforming, and obtains a compact, low-cost, self-sufficient facility suitable for remote locations.

19 Claims, 5 Drawing Sheets

PROCESS FOR CONVERTING GAS TO LIQUIDS

FIELD OF THE INVENTION

The present invention relates to a plant and process for converting associated gas from crude oil into methanol, and more particularly to a plant and process for achieving the conversion at or near the wellhead.

BACKGROUND OF THE INVENTION

In the production of crude oil at remote locations such as, for example, on an offshore deep water platform, producers are confronted with the problem of dealing with gas associated with the crude oil. This gas comprises primarily methane with minor amounts of $C_2$–$C_5$. Simply burning the associated gas in a flare is not attractive either environmentally or economically. The associated gas cannot always be economically or easily liquefied for transport, transported by tanker or pipeline or returned to the reservoir. In such instances, it would be desirable to convert the associated gas into a liquid fuel such as methanol. However, the remote location and space requirements, particularly on deep water production platforms, impose requirements on methanol conversion equipment which have not, as far as applicant is aware, been met by prior art methanol conversion plants. The methanol conversion plant must operate in a small area and cannot have tall equipment because of the potential pitching of the platform or other vessel in which the methanol plant is located. The methanol plant must be able to start up with limited utilities such as electricity and water. In most instances, the plant must also be operable without steam and be self-contained so as not to require supplying any fresh water or electricity. In addition, the methanol plant should be simple to construct from modular units and capable of operation for a long term without attention by a human operator.

As far as applicant is aware there is no plant or process for converting associated gas from crude oil into methanol which satisfies all of these requirements.

SUMMARY OF THE INVENTION

Applicant has invented a process for associated gas conversion into methanol which can be constructed from modular equipment which is not relatively tall and can be erected in a small area. The methanol conversion employs partial oxidation of the associated gas, direct quench/liquid phase methanol synthesis wherein syngas with less that stoichiometric $H_2$:CO is converted to methanol, without the need for separate shift conversion, and a loop purge being used to provide electrical power for the methanol synthesis conversion facility via a gas turbo generator. This associated gas conversion eliminates the complex vapor phase, multiple reactor methanol loop and steam catalytic reforming in favor of liquid phase methanol synthesis and partial oxidation of natural gas, resulting in a compact and low-cost facility suitable for remote locations.

In one aspect, the present invention provides a process for converting associated gas from crude oil into methanol. The process comprises the steps of: (a) conditioning crude oil to separate associated gas from the crude oil; (b) desulfurizing the associated gas from step (a); (c) mixing the desulfurized associated gas from step (b) with oxygen at an elevated temperature to partially oxidize the associated gas and form a syngas stream comprising hydrogen and carbon monoxide; (d) cooling the syngas stream from step (c); (e) contacting the syngas from step (d) with catalyst slurried in an inert liquid to form a product stream containing methanol; (f) condensing methanol from the product stream to form a loop stream essentially free of methanol for recycle to step (e); (g) supplying a purge stream from the loop stream from step (f) for combustion in a gas turbo generator to provide electricity for supplying the oxygen to step (c) and for preheating the associated gas for the partial oxidation in step (c). The desulfurization step (b) can be accomplished simply by passing the associated gas through a ZnO bed. The syngas from the partial oxidation reactor preferably has a substoichiometric hydrogen to carbon monoxide molar ratio, more preferably in the range from about 1.6 to about 2.0 $H_2$:CO, and especially from about 1.7 to 1.8 $H_2$:CO.

The cooling step (d) can be effected by contacting the associated gas with saturated water, e.g. at about 450° F., to quench the syngas to the saturation temperature of the water, and contacting the quenched syngas with relatively cold water to cool the syngas below the water dewpoint to separate and recover the water from the syngas. Cooling to supply the cold water can be provided by indirect heat exchange with sea water. Water for the contacting steps can be from a common reservoir which collects water from the quenching and cooling steps. The process can be operated without any compression equipment, provided the associated gas is supplied at a high enough pressure to overcome the pressure drops in the process steps, except for a recycle compressor to compress the loop stream from step (f) to step (e). The contacting step (e) can also include cooling the inert liquid to maintain an isothermal condition.

The gas turbo generator is preferably designed and sized to provide all of the electricity required by steps (a) through (f), including any associated utilities. If desired, the gas turbo can be designed to operate on dual fuel, i.e. either the relatively low heating value loop purge, or a high heating value natural gas, or a combination thereof. This feature of the invention is particularly attractive during startup operations. In general, the heating value of the purge stream supplied to the gas turbo generator has a heating value from about 100 to about 300 Btu per standard cubic foot, and the natural gas has a heating value of about 800–1100 Btu per standard cubic foot.

In another aspect, the present invention provides a plant for converting associated gas from crude oil into methanol. The plant includes a crude conditioning unit for separating associated gas from the crude oil. A desulfurization unit can be used to remove sulfur compounds and form a desulfurized associated gas stream which is necessary for the subsequent conversion to methanol. A partial oxidation reactor is provided for reacting the desulfurized associated gas stream with oxygen at an elevated temperature to form a syngas stream comprising hydrogen and carbon monoxide. A syngas quench/cooling unit is provided to reduce the temperature of the syngas stream and remove water therefrom. The plant includes a liquid phase methanol reactant comprising catalyst slurried in an inert liquid, a line for introducing the cooled syngas from the quench/cooling unit to a bottom of the methanol reactor with a recycle syngas stream, heat transfer tubes passing through the inert liquid for maintaining isothermal conditions in the methanol reactor and an overhead line for removing product gas from the methanol reactor. A condenser is provided to receive product gas from the overhead line and condense out methanol therefrom to form a recycle gas stream. A purge line is provided to supply a portion of the recycle gas stream to a gas turbo generator to generate sufficient electricity for operation of the plant, preferably without the need for supplying additional electricity from an outside source. A recycle compressor recycles the remaining gas stream to the methanol reactor.

The desulfurization unit preferably comprises a ZnO bed. The partial oxidation reactor is preferably refractory lined. The partial oxidation reactor can be started up simply by preheating the refractory lining to reaction conditions, e.g. about 2500° F. The syngas quench/cooling unit can include a curtain tray saturator and a cooled water contactor. If desired, for example on a deep water drilling platform, a sea water cooler can be used for cooling water supplied to the cooled water contactor. The plant can also include an air separator for supplying an oxygen stream or an oxygen-enriched air stream to the partial oxidation reactor. The gas turbo generator is preferably adapted for operation solely with relatively low value heating gas from the purge line, solely with a relatively high heating value fuel gas, or with a combination of the low and high heating value fuel gases simultaneously. In general, the low heating value is less than 300 Btu per standard cubic foot and the high heating value is greater than 800 Btu per standard cubic foot.

DETAILED DESCRIPTION OF THE INVENTION

Figure 1:
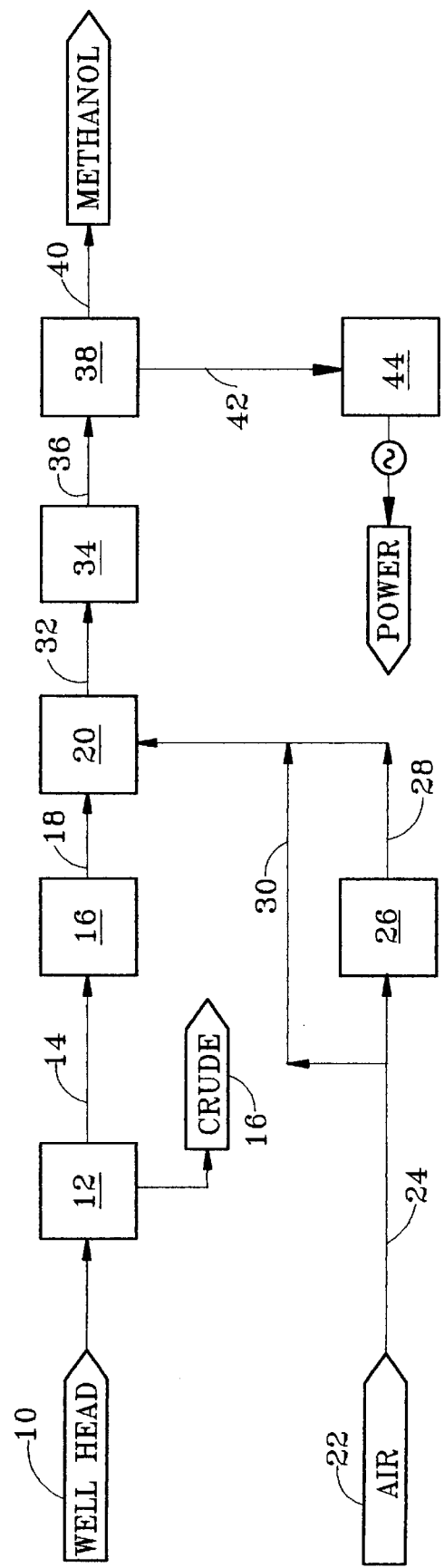
FIG. 1 is a schematic diagram of a conversion of associated gas to methanol according to the present invention.

With reference to FIG. 1, fluids from wellhead 10 are supplied to crude conditioning unit 12 to separate associated gas stream 14 from crude oil product 16. The crude conditioning unit 12 is conventional in the art and does not form a part of the invention per se. All that is necessary is that the associated gas be supplied at a high enough pressure for the subsequent processing steps, preferably at a pressure of about 1000 to 1500 psig, preferably about 1200 psig. The associated gas stream 14 may contain some sulfur compounds such as $H_2S$ and/or mercaptans. These are removed in desulfurization unit 16 to obtain a desulfurized stream 18 for feed to partial oxidation reactor 20. Compressed air source 22 supplies air via line 24 to air separation unit 26 which produces oxygen stream 28 for supply to the partial oxidation reactor 20. If desired, a slipstream of compressed air may be provided via line 30 so that oxygen-enriched air is fed to the partial oxidation reactor 20. Syngas stream 32 from the partial oxidation reactor 20 is quenched and cooled in cooling unit 34. The cooled syngas in line 36 is supplied to liquid methanol synthesis unit 38 which produces methanol stream 40. Purge gas 42 from the liquid methanol synthesis unit 38 is supplied to gas turbo generator 34 which supplies electrical power for the facility.

Figure 2:
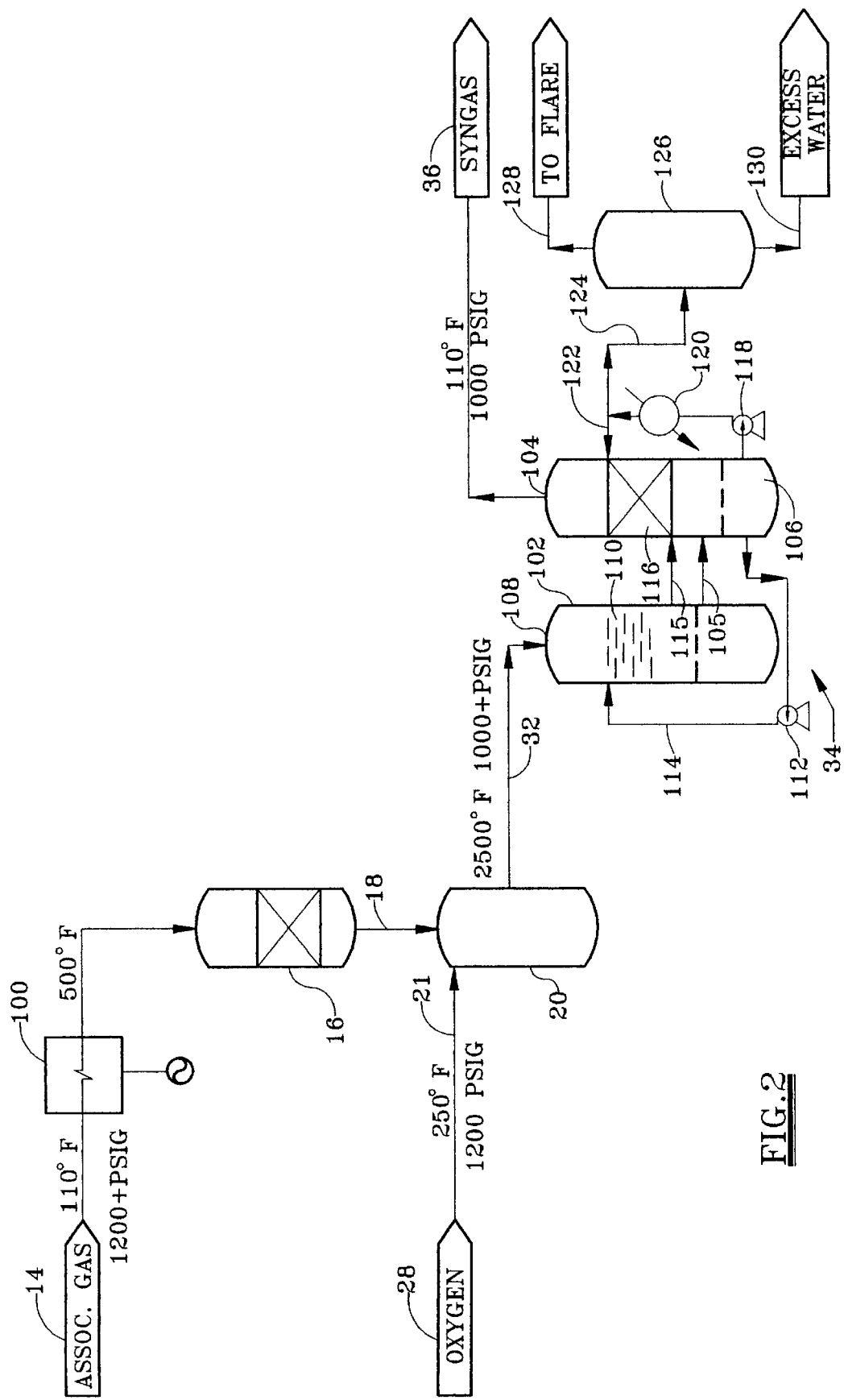
FIG. 2 is a schematic process diagram of desulfurization, partial oxidation and syngas conditioning according to the present invention.

FIG. 2 shows associated gas desulfurization, partial oxidation and syngas conditioning according to one embodiment of the present invention. Associated gas line 14 supplies associated gas at 110° F. and greater than 1200 psig to heater 100 to heat the associated gas to above 500° F. Power for the heater 100 can be supplied by the gas turbo generator 44. For an associated gas feed rate of 35,000 standard cubic feet/minute, heater 100 will require approximately 8200 kw. The heated associated gas is then supplied to desulfurization unit 16 which can be a bed of ZnO which removes any sulfur compounds such as $H_2S$ and/or mercaptans. Desulfurized associated gas is fed through line 18 to partial oxidation reactor 20 along with oxygen from line 21 supplied at about 250° F. and 1200 The partial oxidation reactor 20 is preferably lined with insulating refractory to maintain a temperature of about 2500° F. For startup purposes, the partial oxidation reactor 20 can be equipped with a natural gas burner (not shown) which provides sufficient heat to preheat the refractory to about 2500° F. Then, the oxygen stream 21 and the associated gas from stream 18 are fed to the partial oxidation reactor and the partial oxidation reaction auto-initiates due to the preheated nature of the refractory lining. This greatly simplifies startup. The partial oxidation reactor converts the associated gas to hydrogen and carbon monoxide, but also forms minor amounts of water, carbon dioxide and byproducts.

The partial oxidation reaction products pass from the reactor via line 32 at approximately 2500° F. and 1000–1200 psig to syngas quench/cooling unit 34. The quench/cooling unit 34 preferably comprises a first tower 102 and a second tower 104. Water collecting in the bottom of tower 102 gravity flows via line 105 into the tower 104 where it is collected in bottom compartment 106 which serves as a common tank or reservoir. The first tower 102 has a top inlet 108 for the hot partial oxidation products to enter and a plurality of curtain trays 110 through which the hot gases pass. As the hot gases pass through the curtains of the trays 110, the gases are saturated and cooled to approximately 400–500° F. Water is supplied from the reservoir 106 via pump 112 and line 114. As mentioned above, the water flows from the bottom of tower 102 back into reservoir 106 and the quenched gases flow via line 115 from tower 102 to pass upwardly through the second tower 104. The second tower 104 contains contacting elements 116 such as trays or packing rings. Water is pumped from the reservoir 106 by means of pump 118 through sea water indirect heat exchanger 120 and line 122 to the top of the tower 104. Sufficient sea water is supplied to the cooler 120 to cool the water in line 122 to approximately 80–150° F., typically 110° F. This, in turn, directly cools the gas as it passes up through the contacting elements 116 to about the same temperature as the cooling water, i.e. about 110° F. Thus, the gas exiting the syngas quench/cooling unit 34 has an exit temperature of about 110° F. and a pressure of about 1000 psig. Water from line 122 trickles down through the contacting elements 116 and is collected in the reservoir 106. Excess water formed in the partial oxidation reactor 20 and collected in the reservoir 106 is taken out of the system by means of line 124 which can include a level control valve (not shown) tied to the water level in the reservoir 106. Water in line 124 is sent to degassing unit 126 and any gases evolved are sent via overhead line 128 to a flare (not shown). The degasified, excess water is obtained via line 130 for further processing or disposal.

Figure 3:
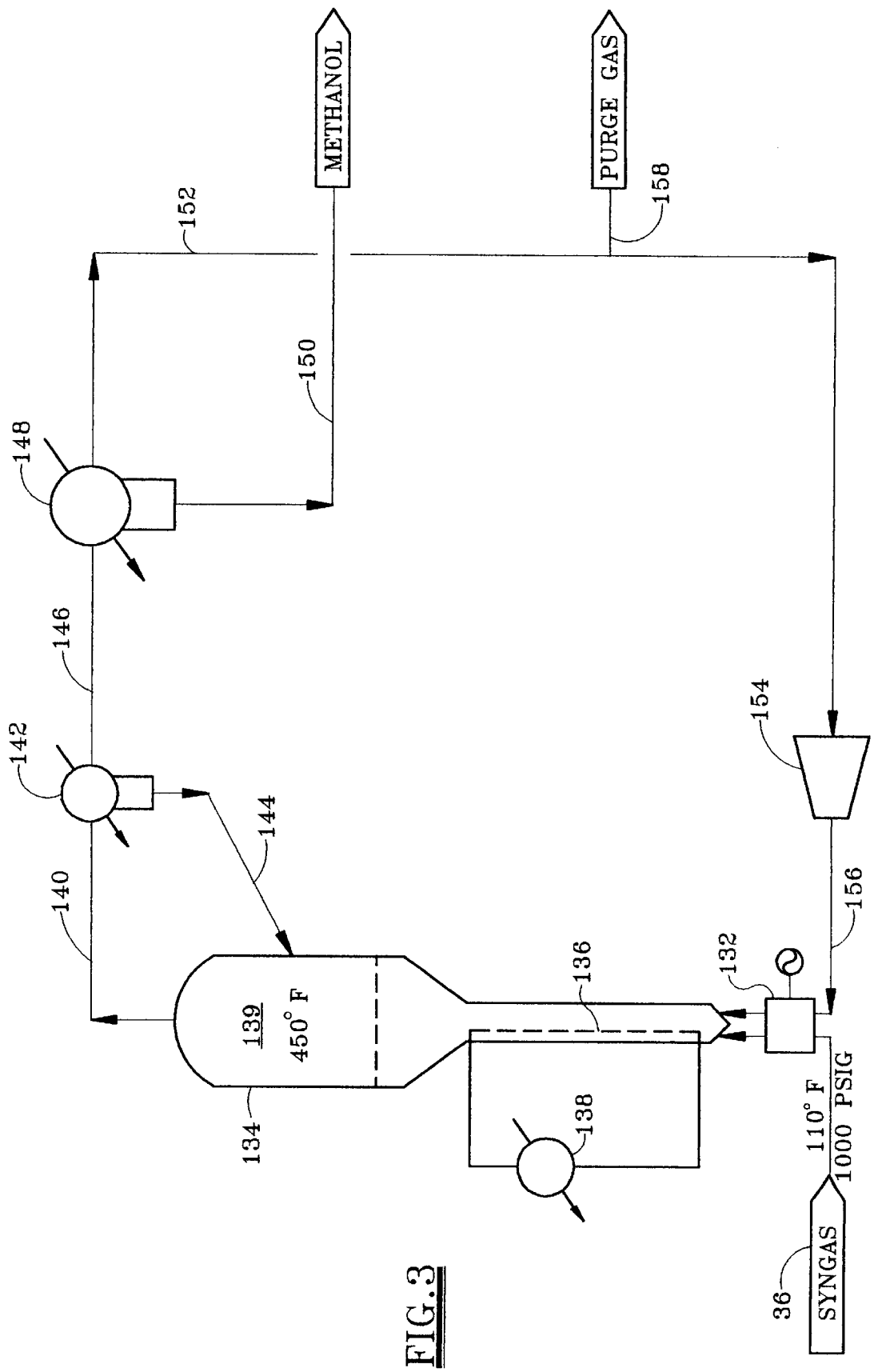
FIG. 3 is a schematic process diagram of the liquid phase methanol synthesis according to the present invention.

FIG. 3 shows a liquid phase methanol conversion process according to one embodiment of the present invention. Syngas via line 36 is passed through heater 132 and introduced to the bottom of 3-phase reactor 134. The reactor 134 includes a liquid phase with solid catalyst slurried therein. The liquid is inert to the syngas and methanol, and is commercially available. The catalyst is the conventional copper based methanol powdered form catalyst. The slurried catalyst/inert liquid is maintained at isothermal conditions by circulating the heat transfer fluid through internal tubing 136 and cooler 138. Cooler 138 is preferably a conventional shell and tube. The heat transfer fluid can be water/steam or a conventional heat transfer fluid. Methanol, nitrogen and unconverted hydrogen and carbon monoxide are collected in a vapor space 139 at the top of the reactor 134 and supplied via line 140 to knock out pot 142 which cools the overhead gases enough to knock out any overflow inert liquid and/or catalyst particles, returned to the reactor 134 via line 144. From knockout pot 142, the product gases flow via line 146 through condenser 148 which condenses out the methanol which is recovered via line 150. The loop gas is then passed via line 152 to recycle compressor 154 and then to preheater 132 via line 156. Purge gas is removed from the loop line 152 via line 158. The methanol produced is fuel grade methanol of about 98% purity with approximately 0.4 weight percent $CO_2$, 0.4 weight percent $H_2O$ and about 1.2 weight percent other organic compounds. The purge gas stream 158 is required to prevent inert gas such as nitrogen from accumulating in the loop stream 152. The loop stream 152 can contain for example, approximately 44 volume percent hydrogen, 42 volume percent carbon monoxide and 14 volume percent nitrogen. The amount of nitrogen in the loop stream 152 can also be influenced by the amount of nitrogen in the oxygen feed line 21 to the partial oxidation reactor 20, (see FIG. 2). The line 21 should contain approximately 45 to 95% oxygen in order to keep the nitrogen level in the loop stream 152 from building up, while simultaneously balancing the amount of purge gas sent to the gas turbo generator 44 such that it is sufficient to provide enough power to run the entire facility without supplemental fuel except at start up.

Figure 4:
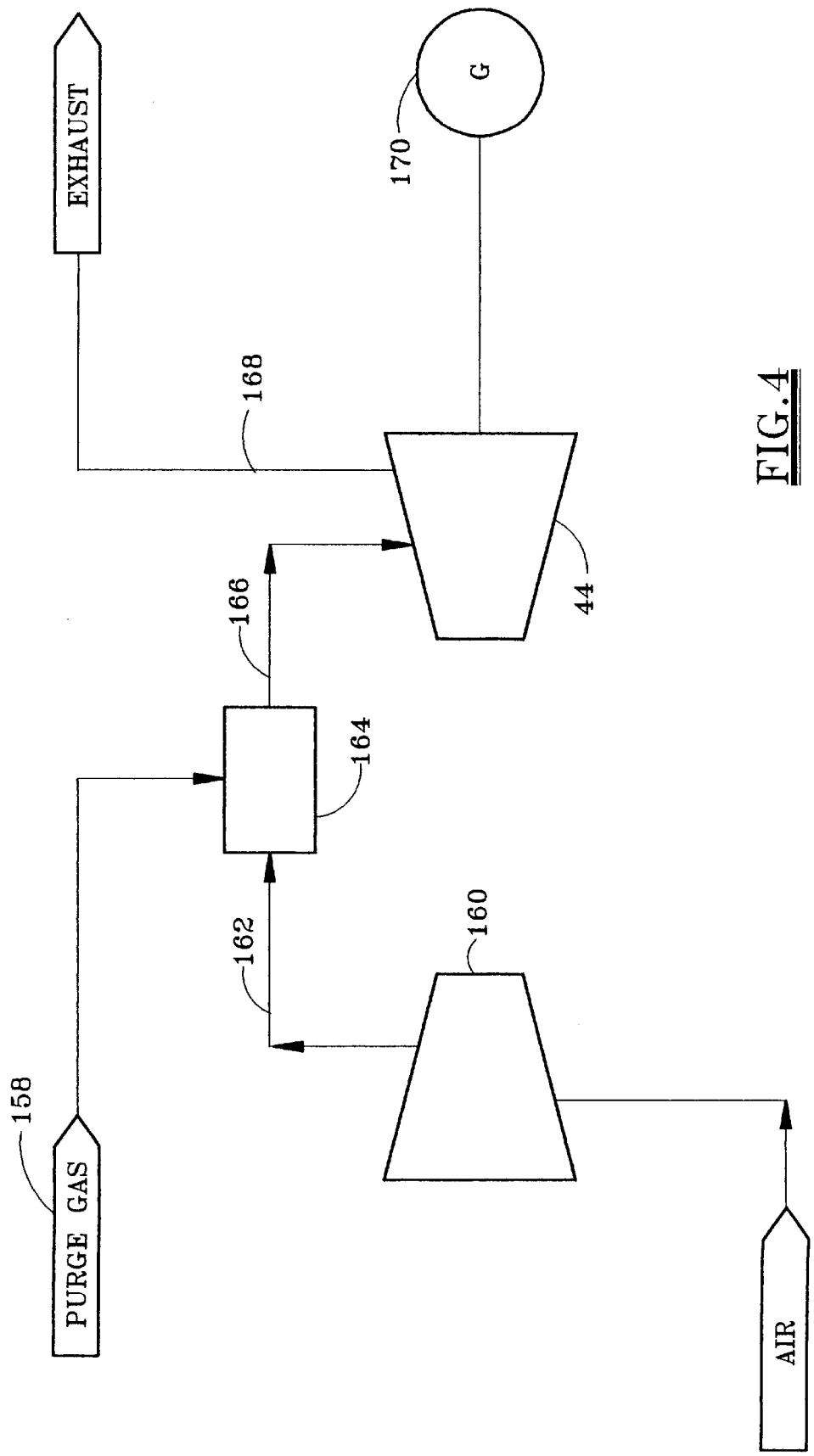
FIG. 4 is a schematic process diagram of the turbo generator used to supply power for the process according to the present invention.

FIG. 4 shows the schematic arrangement of the gas turbo generator 44. Purge gas from line 158 is combined with air supplied via compressor 160 and line 162 to mixing element 164. The combined air/fuel mixture is supplied via line 166 to the suction of gas turbo generator 44 which exhausts the combustion gas via line 168. An electrical generator 170 is connected, for example, by common shaft to the gas turbo generator 44. If desired, the compressor 160 can also be connected via a common shaft to the gas turbo generator 44.

Figure 5:
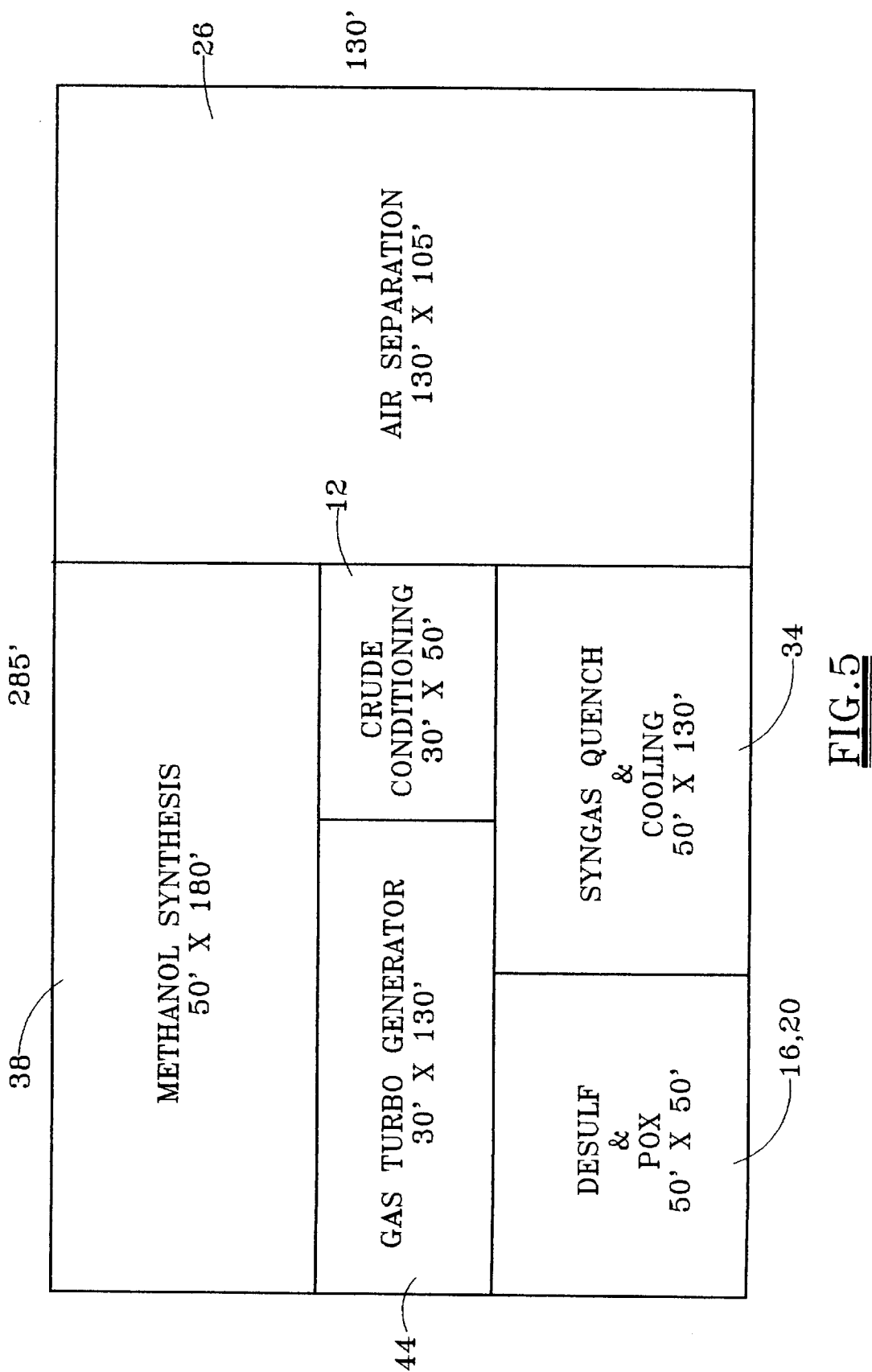
FIG. 5 is a plot plan showing the methanol plant layout and space requirements according to one embodiment of the present invention.

FIG. 5 shows one example of a methanol conversion unit layout in a rectangular area measuring 130'×285'. The crude conditioning unit 12 measures approximately 30'×50'. The desulfurization 16 and partial oxidation 20 can be provided as one modular unit in a 50'×50' area. The air separation unit 26 requires the most room, approximately 130' by 105'. The methanol synthesis reactor 38 requires a plot space of approximately 50'×180'. The syngas cooling unit 34 requires a space of approximately 50'×130'. Finally, the gas turbo generator 44 requires a plot space of approximately 30'×130'. Of course, this is only one hypothetical layout and the actual plot space required can change with the size of the unit, space requirements, and the specific equipment employed.

EXAMPLE

A plant was designed for converting associated gas to methanol in accordance with the principles of the present invention. The design was based on 115,856 lbs per hour of associated gas at 1200 psig and 110° F. with the following dry basis composition:

TABLE 1

| Component | Mole Percent |
| --- | --- |
| $C_1$ | 79.321 |
| $C_2$ | 10.290 |
| $C_3$ | 6.094 |
| $C_4$ | 2.398 |
| $C_{5+}$ | 1.199 |
| $N_2$ | 0.598 |
| $CO_2$ | 0.100 |
| $H_2S$ | trace |

The electrical heater 100 (FIG. 2) preheats the associated gas to 500° F. The sulfur guard bed 16 (FIG. 2) is a conventional ZnO particulate bed which completely removes the sulfur compounds from the associated gas to avoid poisoning the catalyst in reactor 134 (FIG. 3). The desulfurized associated gas is reacted in refractory-lined partial oxidation reactor 20 (FIG. 2) with 95 percent oxygen stream 21 supplied at 250° F. and 1150 psig. The effluent from the reactor 20 is fed to curtain tray quench tower 102 (FIG. 2) where it is cooled to 468° F. The gas then passes through packed ring contactor tower 104 where it is cooled to 110° F. The syngas is then heated by electrical heater 132 to approximately 450° F. and fed to the bottom of the reactor 134. The reactor 134 is kept at isothermal conditions by circulating heat transfer fluid through tubes 136 in the liquid phase of the reactor and shell and tube exchanger 138. The reactor 134 achieves a conversion of about 10% to obtain an overhead stream 140 of the following composition presented in Table 2.

TABLE 2

| Component | Mole Percent |
| --- | --- |
| $H_2$ | 39.925 |
| CO | 34.398 |
| MeOH | 13.907 |
| $CO_2$ | 6.431 |
| $N_2$ | 4.013 |
| $CH_4$ | 0.634 |
| $HCOOCH_3$ | 0.348 |
| $H_2O$ | 0.344 |

Methanol is condensed out and recovered by cooling the overhead stream to about 105° F. The product is approximately 150,728 lbs/hr of methanol of about 98% purity containing about 0.4 weight percent $CO_2$, about 0.4 weight percent water, and about 1.4 weight percent methyl formate and other organic compounds. About 96,950 lbs/hr of purge gas (about 46.5 volume percent $H_2$, 40 volume percent CO, and 12.5 volume percent $N_2$, $CH_4$, $H_2O$, $CO_2$ and MeOH; heating value 270 Btu/standard cubic foot) are supplied to gas turbo generator 44 which converts about 584×10⁶ Btu/hr to about 50 MW. The power is used as follows in Table 3.

TABLE 3

| Operation | Power (MW) |
| --- | --- |
| Air separatation unit 26 | 26 |
| Associated gas preheater 100 | 10 |
| Liquid Methanol reactor unit 38 | 9 |
| Miscellaneous | 4 |
| Syngas cooling unit 34 | 1 |
| Total | 50 |

As seen from Table 3, the gas turbo generator 44 supplies all of the electricity required by the plant.

The above description is representative of the preferred embodiments of the invention and is intended to be illustrative and not limiting. Various changes and modifications of the illustrative embodiments will become apparent to the skilled artisan in view thereof. It is intended that all such variations within the scope or spirit of the appended claims be embraced thereby.

I claim:

1. A process for converting associated gas from crude oil into methanol comprising the steps of:
   (a) conditioning crude oil to separate associated gas from the crude oil;
   (b) desulfurizing the associated gas from step (a);
   (c) mixing the desulfurized associated gas from step (b) with a stream comprising at least about 45 mole percent oxygen at an elevated temperature for once-through partial oxidation of the associated gas to form a syngas stream comprising hydrogen and carbon monoxide;
   (d) cooling the syngas stream from step (c) and condensing water therefrom to form a syngas stream essentially free of water;
   (e) contacting the syngas from step (d) with catalyst slurried in an inert liquid to form a product stream containing methanol;
   (f) condensing fuel grade methanol essentially free of water from the product stream to form a loop stream essentially free of methanol for recycle to step (e);
   (g) supplying a purge stream from the loop stream from step (f) for combustion in a gas turbo generator to provide electricity for supplying the oxygen to step (c) and preheating the associated gas for the partial oxidation in step (c).

2. The process of claim 1 wherein step (b) comprises passing the associated gas through a ZnO bed.

3. The process of claim 1 wherein the syngas has a substoichiometric hydrogen to carbon monoxide molar ratio.

4. The process of claim 3 wherein the molar ratio of hydrogen to carbon monoxide ratio is about 1.6–2.0.

5. The process of claim 1 wherein the cooling step (d) comprises contacting the associated gas with saturated water to quench the syngas to the saturation temperature of the water and contacting the quenched syngas with relatively cold water to cool the syngas below the water dewpoint to separate water from the syngas.

6. The process of claim 5 wherein the cooling step (d) comprises pumping water from a common reservoir to the contacting steps in step (d) and wherein water from the reservoir is cooled in indirect heat exchange with sea water to obtain the relatively cold water.

7. The process of claim 1 wherein the loop stream is compressed for recycle from step (f) to step (e).

8. The process of claim 1 wherein the contacting step (e) includes cooling the inert liquid to maintain an isothermal condition.

9. The process of claim 1 wherein the quantity of the purge stream supplied to the gas turbo generator is balanced such that the electricity produced by the gas turbo generator matches that required for steady state operation of steps (a) through (f).

10. The process of claim 9 comprising supplying natural gas with a heating value of at least 800 Btu per standard cubic foot to the gas turbo generator for startup, and thereafter supplying the purge stream to the gas turbo generator as the sole fuel gas for the steady state operation.

11. The process of claim 9 wherein the heating value of the purge stream supplied to the gas turbo generator has a heating value from about 100 to about 300 Btu per standard cubic foot.

12. A plant for converting associated gas from crude oil into methanol comprising:
   a crude conditioning unit for separating associated gas from the crude oil;
   a desulfurization unit for removing sulfur compounds and forming a desulfurized associated gas stream;
   a partial oxidation reactor for once-through reaction of the desulfurized associated gas stream with a stream comprising at least about 45 mole percent oxygen at an elevated temperature to form a syngas stream comprising hydrogen and carbon monoxide;
   a syngas quench/cooling unit for reducing the temperature of the syngas stream and removing water therefrom;
   a liquid phase methanol reactor comprising catalyst slurried in an inert liquid, a line for introducing the cooled syngas from the syngas quenching/cooling unit to a bottom of the methanol reactor with a recycle syngas stream, heat transfer tubes passing through the inert liquid for maintaining isothermal conditions in said methanol reactor, and an overhead line for removing product gas from said methanol reactor;
   a condenser for receiving product gas from said overhead line and condensing fuel grade methanol essentially free of water therefrom to form a recycle gas stream;
   a purge line for supplying a portion of the recycle gas stream to a gas turbo generator to generate sufficient electricity for steady state operation of the plant;
   a recycle compressor for recycling the remaining recycle gas stream to the methanol reactor.

13. The plant of claim 12 wherein the desulfurization unit comprises a ZnO bed.

14. The plant of claim 12 wherein the partial oxidation reactor is refractory-lined.

15. The plant of claim 12 wherein the syngas quench/cooling unit comprises a curtain tray saturator and a cooled water contactor.

16. The plant of claim 15 including a sea water cooler for cooling water supplied to said cooled water contactor.

17. The plant of claim 12 further comprising an air separator for supplying an oxygen stream or an oxygen-enriched air stream to the partial oxidation reactor.

18. The plant of claim 12 wherein the gas turbo generator is adapted for operation solely with relatively low heating value fuel gas from the purge line, solely with a relatively high heating value fuel gas, or with a combination of the low and high heating value fuel gases simultaneously, wherein the low heating value is from 100 to 300 Btu per standard cubic foot and the high heating value is greater than 800 Btu per standard cubic foot.

19. The plant of claim 18 wherein the gas turbo generator is adapted for operation with a balanced quantity of the low heating value fuel gas from the purge line so that the electricity produced by the gas turbo generator matches the electrical requirements for steady state operation of the plant.

* * * * *